United States Patent [19] [11] 4,200,648
Nuss, Jr. et al. [45] Apr. 29, 1980

[54] METHOD OF TREATMENT

[75] Inventors: George W. Nuss, Jr., Lansdale; Norman J. Santora, Roslyn; George H. Douglas, Malvern, all of Pa.

[73] Assignee: William H. Rorer, Inc., Fort Washington, Pa.

[21] Appl. No.: 942,866

[22] Filed: Sep. 15, 1978

Related U.S. Application Data

[63] Continuation-in-part of Ser. No. 839,960, Oct. 6, 1977.

[51] Int. Cl.² ................. A61K 31/19; A61K 31/24; A61K 31/235
[52] U.S. Cl. ......................... 424/308; 424/309; 424/317
[58] Field of Search ............... 424/308, 309, 319; 260/465 E, 566 R, 566 F; 560/35

[56] References Cited

U.S. PATENT DOCUMENTS

| 3,833,606 | 9/1974 | Mohan | 260/566 F X |
|---|---|---|---|
| 3,862,833 | 1/1975 | Johnson et al. | 260/566 F X |
| 4,047,803 | 9/1977 | Yaguchi et al. | 260/566 F X |
| 4,122,026 | 10/1978 | Osman | 260/566 F X |

OTHER PUBLICATIONS

Kadaba et al., J. Heter. Chem., vol. 4, pp. 301-304, (1967).
Goetz, J. Heter. Chem., vol. 5, pp. 501-507, (1968).
Bellobono et al., Tetrahedran, vol. 25, pp. 57-71, (1969).
Ogata et al., J. Chem. Soc., Perkins Trans, vol. 2, pp. 792-797, (1972).
Favini et al., Gazz. Chim. Ital., vol. 96, pp. 1423-1431, (1966).

Primary Examiner—Stanley J. Friedman
Attorney, Agent, or Firm—Miller & Prestia

[57] ABSTRACT

This invention describes a method of treating inflammation in warm-blooded animals by topically administering an effective amount of a benzylideneaniline derivative, and the compositions therefore.

27 Claims, No Drawings

METHOD OF TREATMENT

BACKGROUND OF THE INVENTION

This application is a continuation-in-part of our co-pending application Ser. No. 839,960, filed Oct. 6, 1977.

SUMMARY OF THE INVENTION

This invention describes the pharmaceutical compositions and method of treating warm-blooded animals for the relief of inflammation and associated symptoms by the topical administration of a benzylideneaniline derivative.

Continuous studies have been carried out during the last decade to develop drugs for topical application which would significantly inhibit the development of inflammation as well as accompanying symptoms. While this effort has been carried out in the steroidal field, there have been few compounds developed which are non-steroidal. While many anti-inflammatory compounds have been found to be effective orally, they have had the drawback of being inactive topically as well as causing various side effects or being effective only on a specific disorder.

We have unexpectedly found that the benzylideneaniline compounds and their derivatives have pharmacological properties which are useful for the relief and inhibition and prevention of inflammation conditions when administered topically.

We have also found that these compounds are effective in the treatment of inflammation and control of arthritic conditions associated with inflammation.

Application Ser. No. 839,960, filed Oct. 6, 1977, discloses certain of the benzylideneanilines which have been found to be effective as topical anti-inflammatory agents.

Co-pending, application Ser. No. 942,868, of Nuss et al, discloses compositions for treating radiation-induced erythemas and for protecting the human skin against the harmful effects of sunlight through the use of certain N-benzylidene aniline compounds.

DESCRIPTION AND PREFERRED EMBODIMENTS

This invention describes new compositions and a method of treating inflammation of the integument in warm-blooded animals by the topical administration of a compound having the structural formula

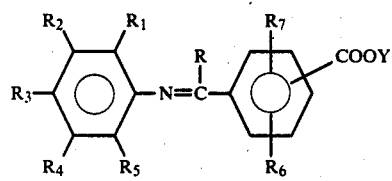

(I)

where:
Y is hydrogen, alkyl, aryl and aralkyl;
R is hydrogen or alkyl;
$R_1$, $R_2$, $R_3$, $R_4$, $R_5$, and $R_6$ may be the same or different and are
hydrogen,
alkyl,
cyano,
nitro,
amino,
haloloweralkoxy,
haloloweralkyl,
halo,
loweralkoxy,
thio,
acylthio,
loweralkylthio,
loweralkylsulfinyl,
loweralkylsulfonyl, and
hydroxy;
$R_3$ may also be cycloalkyl, cycloalkenyl, aryl and heteroloweralkylidenyl;
$R_7$ is hydrogen, hydroxyl, carboxy, carbalkoxy, or halo.

The more preferred compounds for a method of topically treating inflammation embrace those compounds of the Formula II:

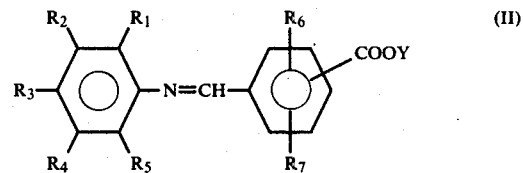

(II)

where:
Y is hydrogen, lower alkyl or phenyl;
$R_1$, $R_2$, $R_4$, $R_5$, and $R_6$ are
hydrogen,
alkyl,
alkoxy,
halo, and
hydroxy;
$R_3$ is
hydrogen,
alkyl,
alkoxy,
halo,
hydroxy,
phenyl, and
cyclohexyl; and
$R_7$ is hydrogen,
carboxy, or
carbalkoxy.

In the descriptive portions of this invention, the following definitions apply:

"alkyl" refers to a loweralkyl hydrocarbon group containing from 1 to about 7 carbon atoms which may be straight chained or branched;

"alkenyl" refers to an unsaturated or partially unsaturated hydrocarbon group containing from 2 to about 7 carbon atoms which may be straight chained or branched;

"cycloalkyl" refers to a hydrocarbon ring having up to about 7 carbon atoms;

"cycloalkenyl" refers to a partially unsaturated hydrocarbon ring having up to about 7 carbon atoms;

"aryl" refers to any benzenoid aromatic group but preferably phenyl;

"acyl" refers to any organic radical derived from an organic acid by the removal of its hydroxyl group such as formyl, acetyl, propionyl, 3-carboxy-2-propenoyl, camphoryl, benzoyl, toluoyl, or heteroyl such as pyridinoyl, piperidonyl, thenoyl, etc.

The compounds of this invention may be prepared by the following general procedures.

Condensation of an aniline derivative with benzaldehyde derivatives or phenyl ketones along the procedures as described by Gillman and Blatt, *Organic Synthesis*, Col. Vol. 1, 2nd Ed., N.Y., John Wiley and Sons, pages 80–81 will result in the desired product.

The following reaction equation illustrates this synthesis:

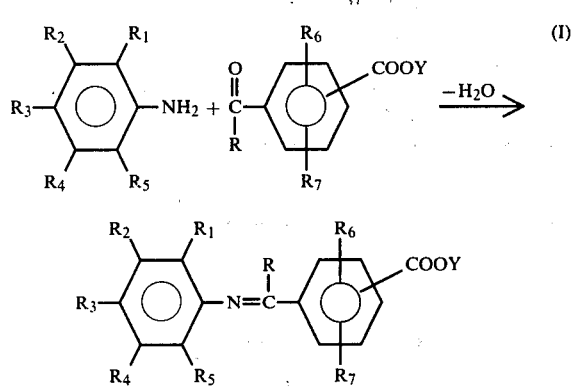

where: Y, R, $R_1$, $R_2$, $R_3$, $R_4$, $R_5$, $R_6$, and $R_7$ are as described above.

An alternate method for the production of certain compounds of Formula I involves the distillation of a product from a neat mixture of an aroyl aldehyde and an aniline derivative at an elevated temperature and under a reduced pressure.

A still further method of preparing certain compounds of Formula I would be by condensation of a hindered aroyl aldehyde and an aniline derivative by the azeotropic removal of water.

Appropriately desired end products having various substituents can be prepared at various stages of synthesis using suitable reactions in order to convert one group to another. Thus, for example, using conventional methods, a halogen group can be treated under Rosenmund Von Braun conditions to the nitrile compound. A nitro can be reduced to an amino which can be alkylated to the dialkylamino substituent. An hydroxy compound can be prepared by demethylation of a methoxy substituent. A Sandmeyer type reaction can be carried out on an amino compound to introduce a chloro, bromo, xanthate, hydroxyl or alkoxyl group. The xanthate can then lead to the mercapto by hydrolysis; this, in turn, can be alkylated to an alkylthio group which can be oxidized to alkylsulfinyl and alkylsulfonyl groups. A thiocyanato group may be removed by catalytic hydrogenation.

In accordance with the present invention, a method of treating inflammation in warm-blooded animals is provided which comprises topically administering to the warm-blooded animals in need of such treatment an effective amount of a compound of Formula I.

As used herein, the term "treatment" is meant to include both active treatment and preventative or prophylactic treatment.

The present invention also has for its object compositions for treating conditions requiring anti-inflammatory treatment containing at least one of the compounds of Formula I in an amount of about 0.05–5.0% by weight of the composition, preferably from about 0.1–1.0% by weight. These compositions can be in the form of a solution, a cream, a powder, gel, ointment, salve, lotion or milk. They can also consitute makeup products or dermatological cakes containing the ingredients standard to these types of compositions.

The following examples will further illustrate the formulations containing the compounds of Formula I but are not to be considered as limiting the scope of this invention.

EXAMPLE 1

N-(p-carbomethoxybenzylidene)-3,5-dichloroaniline p-Carbomethoxybenzaldehyde (0.20 moles) was treated with 3,5-dichloroaniline (0.20 moles) with vigorous stirring in a 1 liter Erlenmeyer Flask. After 15 mins., 33 cc. of 95% ethanol was added and the reaction mixture was stirred vigorously for an additional 5 minutes. The reaction mixture was left standing at room temperature for 10 min.; then it was placed in an ice bath for 0.5 hours. The crystals which formed were collected, washed with 95% ethanol, and air-dried. Recrystallization from 85% ethanol gave N-(p-carbomethoxybenzylidene)-3,5-dichloroaniline.

EXAMPLE 2

N-(o-carboxybenzylidene)aniline o-carboxybenzylaldehyde (0.20 moles) was treated with aniline with vigorous stirring in a 1 liter Erlenmeyer Flask. After 15 min., 33 cc. of 95% ethanol was added and the reaction mixture was stirred vigorously for an additional 5 min. The reaction mixture was left standing at room temperature for 10 min., then it was placed in an ice bath for 0.5 hours. The crystals which formed were collected, washed with 95% ethanol, and air dried. Recrystallization from 85% ethanol yielded N-(o-carboxybenzylidene)aniline.

EXAMPLE 3

N-(o-carbomethoxybenzylidene)-3-chloro-2-methylaniline o-carbomethoxybenzylaldehyde (0.20 moles) was treated with 3-chloro-2-methylaniline (0.20 moles) with vigorous stirring in a 1 liter Erlenmeyer Flask. After 15 mins., 33 cc. of 95% ethanol was added and the reaction mixture was stirred vigorously for an additional 5 mins. The reaction mixture was left standing at room temperature for 10 mins., then it was placed in an ice bath for 0.5 hours. The crystals which formed were collected washed with 95% ethanol and air dried. Recrystallization from 85% ethanol gave N-(o-carbomethoxybenzylidene)-3-chloro-2-methylaniline.

EXAMPLE 4

N-(p-carbobutoxybenzylidene)-2-methyl-4-chloroaniline 2-methyl-4-chloroaniline (0.25 moles) and p-carbobutoxybenzaldehyde (0.25 moles) were ground in a mortar. The mixture was heated, with stirring in a water bath for 1.5 hours. Distillation at reduced pressure gave N-(p-carbobutoxybenzylidene)-2-methyl-4-chloroaniline.

EXAMPLE 5

N-(o-carboxybenzylidene)-p-toluidine p-toluidine (0.20 moles), o-carboxybenzaldehyde (0.20 moles), and IRC-50 (weakly acidic) ion exchange resin (0.5 g.) were azeotropically refluxed in toluene (150 cc.). The required amount of water had been removed after 3 hours. The solvent was removed on the rotary, and the residue was distilled under reduced pressure to give N-(o-carboxybenzylidene)-p-toluidine.

EXAMPLE 6

N-(p-carbomethoxybenzylidene)-2-methyl-3-chloroaniline p-carbomethoxybenzaldehye (0.20 moles) was treated with 2-methyl-3-chloroaniline (0.20 moles) with vigorous stirring in a 1 liter Erlenmeyer flask. After 15 mins., 33 cc of 95% ethanol was added and the reaction mixture was stirred vigorously for an additional 45 mins. The reaction mixture was left standing at room temperature for 10 min., then it was placed in an ice bath for 0.5 hours. The crystals which formed were collected, washed with 95% ethanol, and air dried. Recrystallization from 95% ethanol gave N-(p-carbomethoxybenzylidene)-2-methyl-3-chloroaniline.

EXAMPLE 7

N-(p-carboxybenzylidene)-2-methyl-3-chloroaniline 2-methyl-3-chloroaniline (0.25 moles) and p-carboxybenzaldehyde (0.25 moles) were ground in a mortar. The mixture was heated, with stirring in a water bath for 1.5 hours. Distillation at reduced pressure gave N-(p-carboxybenzylidene)-2-methyl-3-chloroaniline as a second fraction.

EXAMPLE 8

N-(p-carbomethoxybenzylidene)-p-methylaniline p-toluidine (0.20 moles), p-carbomethoxybenzaldehyde (0.20 moles), and IRC-50 (weakly acidic) ion exchange resin (0.5 g.) were azeotropically refluxed in toluene (150 cc.). The required amount of water had been removed after 3 hours. The solvent was removed on the rotary evaporator and the residue was recrystallized with 95% ethanol to yield N-(p-carbomethoxybenzylidene)-p-methylaniline.

EXAMPLE 9

N-(o-carboxybenzylidene)-2,3-dichloroaniline 8.1 g. (0.05 moles) of 2,3-dichloroaniline was added to 0.05 moles of o-carboxybenzaldehyde. The reaction vessel and contents were thereafter allowed to stand at room temperature for 4 hours. During this period, the reaction mixture became a solid crystalline mass. The latter was dissolved in hot benzene and thereafter cooled to room temperature whereupon the N-(o-carboxybenzylidene)-2,3-dichloroaniline product precipitated as a crystalline solid and was recovered by filtration. This product was washed with a petroleum hydrocarbon fraction boiling at from 86° to 100° C. (Skellysolve) and air dried.

EXAMPLE 10

N-(p-carboxybenzylidene)-3,5-dichloroaniline

To a reaction flask, equipped with a Dean-Stark trap, is added 3,5-dichloroaniline (16.2 g., 0.10 mole), p-carboxybenzaldehyde (0.10 moles), p-toluenesulfonic acid monohydrate (0.2 g), and toluene (100 ml.). The reaction mixture is then warmed to reflux and the water (1.65 ml.) collected by azeotroping. The cooled reaction mixture is treated with charcoal and the filtrate reduced to vacuo to give an amber oil that crystallizes on standing to give N-(p-carboxybenzylidene)-3,5-dichloroaniline which is recrystallized from pentane.

EXAMPLE 11

N-(p-carboxybenzylidene)-3,4-dichloroaniline

Equimolar amounts of 3,4-dichloroaniline and p-carboxybenzaldehyde are stirred together at room temperature to give a nearly quantitative yield of N-(p-carboxybenzylidene)-3,4-dichloroaniline that is recrystallized from ethanol.

EXAMPLE 12

Following the procedures of Examples 1-11, the following compounds may also be prepared:

N-(o-carbomethoxybenzylidene)aniline
N-(m-carbomethoxybenzylidene)aniline
N-(p-carbomethoxybenzylidene)aniline
N-(carboxybenzylidene)toluidine
N-(carbophenoxybenzylidene)toluidine
N-(carboethoxybenzylidene)toluidine
N-(o-carboxybenzylidene)-α,α,α-trifluorotoluidine
N-(o-carbomethoxybenzylidene)-α,α,α-trifluorotoluidine
N-(carboxybenzylidene)ethylaniline
N-(carbomethoxybenzylidene)hydroxyaniline
N-(carboethoxybenzylidene)hydroxyaniline
N-(carbopropoxybenzylidene)hydroxyaniline
N-(2,3-dicarboxybenzylidene)aniline
N-(2,4-dicarboxybenzylidene)aniline
N-(2,5-dicarboxybenzylidene)aniline
N-(2,6-dicarboxybenzylidene)aniline
N-(3,4-dicarboxybenzylidene)-o-hydroxyaniline
N-(3,5-dicarboxybenzylidene)-o-hydroxyaniline
N-(carboxybenzylidene)fluoroaniline
N-(carbomethoxybenzylidene)fluoroaniline
N-(carboethoxybenzylidene)fluoroaniline
N-(carbopropoxybenzylidene)fluoroaniline
N-(carbophenoxybenzylidene)fluoroaniline
N-(p-carbomethoxybenzylidene)-m-fluoroaniline
N-(o-carbomethoxybenzylidene)-p-fluoroaniline
N-(m-carbomethoxybenzylidene)-p-fluoroaniline
N-(p-carbomethoxybenzylidene)-p-fluoroaniline
N-(o-carbophenoxybenzylidene)-2-bromoaniline
N-(m-carbophenoxybenzylidene)-2-bromoaniline
N-(p-carbobenzyloxybenzylidene)-2-iodoaniline
N-(o-carbobenzyloxybenzylidene)-2-iodoaniline
N-(m-carbobenzyloxybenzylidene)-2-iodoaniline
N-(p-carbobenzyloxybenzylidene)-3-iodoaniline
N-(p-carbophenoxybenzylidene)-p-chloroaniline
N-(p-carbophenoxybenzylidene)-2-chloroaniline
N-(o-carbobenzyloxybenzylidene)-3-chloroaniline
N-(m-carbophenoxybenzylidene)-3-chloroaniline
N-(p-carbobenzylbenzylidene)-3-chloroaniline
N-(o-carbophenoxybenzylidene)-3-chloroaniline
N-(m-carbobenzyloxybenzylidene)-3-chloroaniline
N-(p-carbophenoxybenzylidene)-3-fluoroaniline
N-(p-carbobenzyloxybenzylidene)-p-fluoroaniline
N-(2,3-dicarbomethoxybenzylidene)-p-hydroxyaniline
N-(2,4-dicarboxymethoxybenzylidene)-p-hydroxyaniline
N-(2,5-dicarbomethoxybenzylidene)-p-hydroxyaniline
N-(2,6-dicarbomethoxybenzylidene)-p-hydroxyaniline
N-(3,4-dicarbomethoxybenzylidene)-p-hydroxyaniline
N-(3,5-dicarbomethoxybenzylidene)-p-hydroxyaniline
N-(2,3-dicarboethoxybenzylidene)-p-hydroxyaniline
N-(2,4-dicarboethoxybenzylidene)-p-hydroxyaniline
N-(carboxybenzylidene)chloroaniline
N-(carbomethoxybenzylidene)chloroaniline N-(carboethoxybenzylidene)chloroaniline
N-(carboxybenzylidene)-2,3-dichloroaniline
N-(carbomethoxybenzylidene)-2,4-dichloroaniline
N-(carboethoxybenzylidene)-2,5-dichloroaniline
N-(p-carbomethoxybenzylidene)-2,6-dichloroaniline
N-(p-carbomethoxybenzylidene)-3,4-dichloroaniline
N-(p-carbomethoxybenzylidene)-3,5-dichloroaniline
N-(p-carbomethoxybenzylidene)-2,3,4-trichloroaniline
N-(p-carbomethoxybenzylidene)-2,4,6-trichloroaniline
N-(p-carboxybenzylidene)-4-toluidine
N-(p-carboxybenzylidene)-2,3-difluoroaniline
N-(p-carbomethoxybenzylidene)-2,4-difluoroaniline
N-(p-carboxybenzylidene)-2,5-difluoroaniline
N-(p-carboxybenzylidene)-2,6-difluoroaniline
N-(p-carbomethoxybenzylidene)-3,4-difluoroaniline
N-(p-carbomethoxybenzylidene)-3,5-difluoroaniline
N-(p-carbomethoxybenzylidene)-p-trifluoromethylaniline
N-(p-carboxybenzylidene)-2,3,4-trifluoroaniline
N-(p-carboxybenzylidene)-2,4,6-trifluoroaniline
N-(p-carboxybenzylidene)-p-methylsulfonylaniline
N-(p-carbomethoxybenzylidene)-p-methylsulfonylaniline
N-(o-carboxybenzylidene)-2-methyl-3-chloroaniline
N-(p-carboxybenzylidene)-2-methyl-3-chloroaniline
N-(o-carbomethoxybenzylidene)-2-methyl-3-chloroaniline
N-(p-carbomethoxybenzylidene)-2-methyl-3-chloroaniline
N-(p-carbomethoxybenzylidene)-p-methylsulfinylaniline
N-(p-carboxybenzylidene)-2-trifluoromethyl-4-fluoroaniline
N-(o-carboxybenzylidene)-2-trifluoromethyl-4-fluoroaniline
N-(o-carbomethoxybenzylidene)-2-trifluoromethyl-3-fluoroaniline
N-(p-carbomethoxybenzylidene)-2-trifluoromethyl-3-fluoroaniline
N-(p-carbomethoxybenzylidene)-p-aniline
N-(p-carboxybenzylidene)-2-aminoaniline
N-(p-carboxybenzylidene)-p-aminoaniline
N-(p-carbomethoxybenzylidene)-2-methyl-4-cyanoaniline
N-(p-carbomethoxybenzylidene)-2-methyl-4-nitroaniline
N-(p-carboxybenzylidene)-2,4-dinitroaniline
N-(3-carboxy-4-cyclohexylbenzylidene)aniline
N-(3-carbomethoxy-4-cyclohexylbenzylidene)aniline
N-(p-carbomethoxybenzylidene)biphenyl-4-amine
N-(p-carboxybenzylidene)biphenyl-4-amine
N-(p-carbomethoxybenzylidene)-3-nitro-biphenyl-4-amine
N-(p-carboxybenzylidene)-3-chloro-biphenyl-4-amine
N-(p-carbomethoxybenzylidene)-3-fluoro-biphenyl-4-amine
N-(p-carboxybenzylidene)-2-methyl-biphenyl-4-amine
N-(p-carbomethoxybenzylidene)-2,3-xylidine
N-(p-carbomethoxybenzylidene)-2,4-xylidine
N-(2,5-carboxybenzylidene)fluoroaniline
N-(2,6-dicarboxybenzylidene)fluoroaniline
N-(3,4-dicarboxybenzylidene)fluoroaniline
N-(3,5-dicarboxybenzylidene)fluoroaniline
N-(2,5-dicarbomethoxybenzylidene)fluoroaniline
N-(2,6-dicarbomethoxybenzylidene)fluoroaniline
N-(2,3-dicarboxybenzylidene)chloroaniline
N-(2,4-carboxybenzylidene)chloroaniline
N-(2,5-dicarboxybenzylidene)chloroaniline
N-(2,6-dicarboxybenzylidene)chloroaniline
N-(3,4-dicarboxybenzylidene)chloroaniline
N-(3,5-dicarboxybenzylidene)chloroaniline
N-(p-carboxybenzylidene)-m-methoxyaniline
N-(p-carbomethoxybenzylidene)-m-ethoxyaniline
N-(2,3-dicarbomethoxybenzylidene)-p-methoxyaniline
N-(2,4-dicarboethoxybenzylidene)-p-ethoxyaniline
N-(2,5-dicarboxybenzylidene)-p-hydroxyaniline
N-(2,6-dicarboxybenzylidene)-p-hydroxyaniline
N-(o-carboxybenzylidene)-p-bromoaniline
N-(2,4-dicarboxybenzylidene)-p-bromoaniline
N-(dicarboxybenzylidene)-2-methyl-3-chloroaniline
N-(dicarboxybenzylidene)-2-methyl-4-chloroaniline
N-(dicarbomethoxybenzylidene)-2-methyl-3-fluoroaniline
N-(dicarbomethoxybenzylidene)-2-methyl-4-fluoroaniline
N-(2,3-dicarboxybenzylidene)-2-methyl-3-chloroaniline
N-(2,4-dicarboxybenzylidene)-2-methyl-4-chloroaniline
N-(2,6-dicarboxybenzylidene)-2-methyl-5-chloroaniline
N-(2,3-dicarbomethoxybenzylidene)-2-methyl-3-chloroaniline
N-(2,4-dicarbomethoxybenzylidene)-2-methyl-4-chloroaniline
N-(2,6-dicarbomethoxybenzylidene)-2-methyl-3-chloroaniline
N-(2,6-dicarbomethoxybenzylidene)-2-methyl-4-chloroaniline
N-(2,4-dicarbomethoxybenzylidene)-2-methyl-5-chloroaniline
N-(2,4-dicarboxybenzylidene)-2,4-dichloroaniline
N-(p-carbomethoxybenzylidene)mesidine
N-(p-carboxybenzylidene)mesidine
N-(p-carbomethoxybenzylidene)-2,4-dibromoaniline
N-(p-carboxybenzylidene)-2,4-dibromoaniline
N-(p-carbomethoxybenzylidene)-2-methyl-4-iodoaniline

EXAMPLE 13

A cream was prepared as follows:

| | |
|---|---|
| N-(2,4-dicarbomethoxybenzylidene)-3,5-dichloroaniline | 0.5 g. |
| Titanium oxide | 10.0 g. |
| Red iron oxide | 0.3 g. |
| Yellow iron oxide | 0.2 g. |
| Brown iron oxide | 0.4 g. |
| Chestnut iron oxide | 0.2 g. |

Several stearyl alcohols oxyethylenated with 33 moles of:

| | |
|---|---|
| Ethylene oxide | 7.0 g. |
| Polyglycol stearate | 6.0 g. |
| Propyl parahydroxybenzoate | 0.2 g. |
| Water, Q.S.P. | 100.0 g. |

Other creams identical to that described immediately above are prepared by replacing N-(2,4-dicarbomethoxybenzylidene)-3,5-dichloroaniline compound with any of the previously-mentioned active compounds.

EXAMPLE 14

A dermatological cleansing cake is prepared by mixing together the following components:
Esters of sodium isothionate and coprafatty acids (sold under the tradename "IGEPON A" having the formula R—COO—CH$_2$—CH$_2$—SO$_3$—Na, wherein R equals fatty acid derivatives having 12-15 carbon atoms)
Lanolin derivative
N-(p-carboxybenzylidene)-2-methyl-4-chloroaniline Other dermatological cleansing cakes, identical to the above, are prepared by replacing N-(p-carboxybenzylidene)-2-methyl-4-chloroaniline with any one of the aforementioned active compounds.

EXAMPLE 15

A powder comprising the following mixture:

| Talc | 99.6 g. |
|---|---|
| Glycerine trioleate | 3.0 g. |
| Isopropyl myristate | 7.0 g. |
| N-(p-carbomethoxybenzylidene)-2-methyl-3-chloroaniline | 0.5 g. |
| Perfume | 2.0 cc. |

Other equally effective powder compositions identical to the above are prepared except that the active ingredient N-(p-carbomethoxybenzylidene)-2-methyl-3-chloroaniline is replaced by any of the other aforementioned active compounds.

EXAMPLE 16

An anti-inflammatory composition in mild form having the following composition:

| Hydrogenated, ethoxylate (10 mol.) lanolin | 1.8 g. |
|---|---|
| Triglyceride of fatty acid of coconut | 7.0 g. |
| Cetylalcohol | 0.6 g. |
| Stearylalcohol | 0.6 g. |
| Paraffin oil (lightweight) | 5.0 g. |
| N-(p-carboxybenzylidene)-p-toluidine | 0.75 g. |
| Stearic acid | 3.0 g. |
| Demineralized water | 72.2 g. |
| Triethanolamine | 0.8 g. |
| Perfume | 0.5 g. |
| Carboxyvinylpolymer | 2.0 g. |
| Conservation agent | 2.0 g. | was manufactured as follows:

A mixture of 1.8 g. hydrogenated, ethoxylated (10 mol.) lanolin, 7.0 g. triglyceride of fatty acid of coconut, 0.6 g. cetyl-alcohol, 0.6 g. stearyl alcohol, 5.0 g. paraffin oil, 0.05 g. hydrocortisone and 3.0 g. of stearic acid was blended at 70° C. After addition of 0.75 g. N-(p-carboxybenzylidene)-p-toluidine, 2.0 g. carboxyvinylpolymer in 72.2 g. demineralized water were added at 70° C. with stirring to the resulting suspension. The mixture was stirred for 15 minutes and then cooled. 0.8 g. of triethanolamine and 0.5 g. of perfume were added at 60° C. and 45° C., respectively. The resulting mixture was stirred until cold and a white milk, which was stable at 3,000 rpm for one hour was obtained. Viscosity: 6,000 Cp (Brockfield, Spindel, 5, 10 rpm).

EXAMPLE 17

0.5 g. of N-(2,4-dicarboxybenzylidene)-3-chloro-2-methylaniline and 0.20 g. N-(p-carbomethoxybenzylidene)-2-methyl-3-chloroaniline are predispersed in 30.0 g. of propylene glycol. The mixture is then homogenized into 97.4 g. of finished cream, ointment or lotion following a modification of any one of the procedures described in F. W. Martin et al, *Remington's Pharmaceutical Sciences*, 14th Ed., Mack Publishing Co., Easton, Pa. (1965).

We claim:
1. A method of treating inflammation in warm-blooded animals which comprises topically administering to an animal in need of said treatment an effective amount of an active compound of the formula

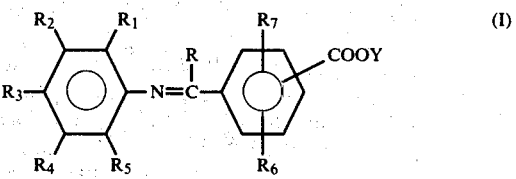

where:
  Y is hydrogen, alkyl or phenyl,
  R is hydrogen, alkyl, or phenyl;
  R$_1$, R$_2$, R$_3$, R$_4$, R$_5$, and R$_6$ may be the same or different and are
    hydrogen,
    alkyl,
    nitro,
    amino,
    haloloweralkoxy,
    haloloweralkyl,
    halo,
    loweralkoxy, and
    hydroxy;
  R$_3$ may also be cycloalkyl, cycloalkenyl or aryl, and
  R$_7$ is hydrogen, hydroxyl, carboxy, carbalkoxy, or halo.

2. The method of topically treating inflammation in warm-blooded animals according to claim 1 where the compound administered is N-(p-carbomethoxybenzylidene)-3,5-dichloroaniline.

3. The method of topically treating inflammation in warm-blooded animals according to claim 1 where the compound administered is N-(p-carbomethoxybenzylidene)-3,4-dichloroaniline.

4. The method of topically treating inflammation in warm-blooded animals according to claim 1 wherein the compound administered is N-(p-carboxybenzylidene)-3,5-dichloroaniline.

5. The method of topically treating inflammation in warm-blooded animals according to claim 1 where the compound administered is N-(p-carboxybenzylidene)-3,4-dichloroaniline.

6. The method of topically treating inflammation in warm-blooded animals according to claim 1 where the compound administered is N-(p-carboxybenzylidene)-2,4-dichloroaniline.

7. The method of topically treating inflammation in warm-blooded animals according to claim 1 where the compound administered is N-(p-carboxybenzylidene)-2,3-dichloroaniline.

8. The method of topically treating inflammation in warm-blooded animals according to claim 1 where the compound administered is N-(p-carboxybenzylidene)-3,5-dichloroaniline.

9. The method of topically treating inflammation in warm-blooded animals according to claim 1 where the compound administered is N-(2,4-dicarboxybenzylidene)aniline.

10. The method of topically treating inflammation in warm-blooded animals according to claim 1 where the compound administered is N-(2,4-dicarbomethoxybenzylidene)aniline.

11. The method of topically treating inflammation in warm-blooded animals according to claim 1 where the compound administered is N-(p-carboxybenzylidene)-2-methyl-3-chloroaniline.

12. The method of topically treating inflammation in warm-blooded animals according to claim 1 where the compound administered is N-(p-carboxybenzylidene)-2-chloro-3-methylaniline.

13. The method of topically treating inflammation in warm-blooded animals according to claim 1 where the compound administered is N-(p-carboxybenzylidene)-2,3-dimethylaniline.

14. The method of topically treating inflammation in warm-blooded animals according to claim 1 where the compound administered is N-(p-carboxybenzylidene)-p-fluoroaniline.

15. The method of topically treating inflammation in warm-blooded animals according to claim 1 where the compound administered is N-(p-carbomethoxybenzylidene)-4-chloroaniline.

16. The method of topically treating inflammation in warm-blooded animals according to claim 1 where the compound administered is N-(p-carboxybenzylidene)-p-bromoaniline.

17. The method of topically treating inflammation in warm-blooded animals according to claim 1 where the compound administered is N-(2,4-dicarboxybenzylidene)-p-fluoroaniline.

18. The method of topically treating inflammation in warm-blooded animals according to claim 1 where the compound administered is N-(p-carbomethoxybenzylidene)-p-bromoaniline.

19. The method of topically treating inflammation in warm-blooded animals according to claim 1 where the compound administered is N-(p-carboxybenzylidene)-biphenyl-4-amine.

20. The method of topically treating inflammation in warm-blooded animals according to claim 1 where the compound administered is N-(p-carbomethoxybenzylidene)-p-methoxyaniline.

21. The method of topically treating inflammation in warm-blooded animals according to claim 1 where the compound administered is N-(2-chloro-4-carboxybenzylidene)-2-methyl-3-chloroaniline.

22. The method of topically treating inflammation in warm-blooded animals according to claim 1 where the compound administered is N-(2-chloro-4-carboxybenzylidene)-2-methyl-4-chloroaniline.

23. The method of topically treating inflammation in warm-blooded animals according to claim 1 where the compound administered is N-(3-carboxy-4-cyclohexylbenzylidene)-4-fluoroaniline.

24. The method of topically treating inflammation in warm-blooded animals according to claim 1 where the compound administered is N-(3-carboxy-4-cyclohexylbenzylidene)-4-bromoaniline.

25. The method of topically treating inflammation in warm-blooded animals according to claim 1 where the compound administered is N-(p-carboxybenzylidene)-o-toluidine.

26. The method of topically treating inflammation in warm-blooded animals according to claim 1 where the compound administered is N-(p-carboxybenzylidene)-4-fluoro-2-trifluoromethylaniline.

27. The method of topically treating inflammation in warm-blooded animals according to claim 1 where the compound administered is N-(p-carbomethoxybenzylidene)-4-fluoro-2-trifluoromethylaniline.

* * * * *